(12) United States Patent  (10) Patent No.: US 8,192,420 B2
Morriss et al.  (45) Date of Patent: Jun. 5, 2012

(54) IONTOPHORESIS METHODS (75) Inventors: John Morriss, San Francisco, CA (US);
Greg Liu, Sunnyvale, CA (US); Kate Hames, San Francisco, CA (US)

(73) Assignee: Acclarent, Inc., Menlo Park, CA (US)

( * ) Notice: Subject to any disclaimer, the term of this patent is extended or adjusted under 35 U.S.C. 154(b) by 213 days.

(21) Appl. No.: 11/962,063

(22) Filed: Dec. 20, 2007

(65) Prior Publication Data
US 2009/0163848 A1 Jun. 25, 2009

(51) Int. Cl.
*A61M 31/00* (2006.01)
*A61N 1/30* (2006.01)

(52) U.S. Cl. .......................................... 604/501; 604/20

(58) Field of Classification Search ..................... 604/20, 604/500, 501, 512
See application file for complete search history.

(56) References Cited

U.S. PATENT DOCUMENTS

| | | |
|---|---|---|
| 858,673 A | 7/1907 | Roswell |
| 3,741,197 A | 6/1973 | Sanz et al. |
| 3,897,786 A | 8/1975 | Garnett et al. |
| 3,913,584 A | 10/1975 | Walchle et al. |
| 3,948,271 A | 4/1976 | Akiyama |
| 3,991,755 A * | 11/1976 | Vernon et al. .................... 604/20 |
| 4,468,218 A | 8/1984 | Armstrong |
| 4,473,073 A | 9/1984 | Darnell |
| 4,564,009 A | 1/1986 | Brinkhoff |
| 4,712,537 A | 12/1987 | Pender |
| 4,971,076 A | 11/1990 | Densert et al. |
| 5,026,378 A | 6/1991 | Goldsmith, III |
| 5,044,373 A | 9/1991 | Northeved et al. |
| 5,053,040 A | 10/1991 | Goldsmith, III |
| 5,254,120 A | 10/1993 | Cinberg et al. |
| 5,261,903 A * | 11/1993 | Dhaliwal et al. .............. 604/416 |
| D352,780 S | 11/1994 | Glaeser et al. |
| 5,421,818 A | 6/1995 | Arenberg |
| 5,466,239 A | 11/1995 | Cinberg et al. |
| 5,496,329 A | 3/1996 | Reisinger |
| D378,611 S | 3/1997 | Croley |
| 5,643,280 A | 7/1997 | Del Rio et al. |

(Continued)

FOREIGN PATENT DOCUMENTS

DE 19618585 11/1997

(Continued)

OTHER PUBLICATIONS

Comeau, M and Brummett, R, Anesthesia of the Human Tympanic Membrane by Iontophoresis of a Local Anesthetic, Feb. 1978, Wiley-Blackwell, 88(2 Pt 1); 277-785.*

(Continued)

*Primary Examiner* — Jackie Ho
*Assistant Examiner* — Imani Hayman
(74) *Attorney, Agent, or Firm* — Steptoe & Johnson LLP (57) ABSTRACT

A method of anesthetizing a tympanic membrane of an ear of a patient using iontophoresis is disclosed. The method involves delivering an anesthetizing drug solution to an ear canal of the patient's ear, wherein the drug solution includes an anesthetic and a buffer, and wherein the drug solution has a pH in the range of about 6.5 to about 7.5; and applying an amount of current to the drug solution, wherein the amount of applied current is increased at a rate of less than about 0.5 milliamp per second until a maximum current is achieved.

34 Claims, 4 Drawing Sheets

U.S. PATENT DOCUMENTS

| | | | |
|---|---|---|---|
| 5,674,196 | A | 10/1997 | Donaldson et al. |
| D387,863 | S | 12/1997 | Herman et al. |
| 5,792,100 | A | 8/1998 | Shantha |
| 5,827,295 | A | 10/1998 | Del Rio et al. |
| 5,893,828 | A | 4/1999 | Uram |
| D418,223 | S | 12/1999 | Phipps et al. |
| D420,741 | S | 2/2000 | Croley |
| 6,045,528 | A | 4/2000 | Arenberg et al. |
| D424,197 | S | 5/2000 | Sydlowski et al. |
| D426,135 | S | 6/2000 | Lee |
| 6,137,889 | A | 10/2000 | Shennib et al. |
| 6,183,469 | B1 | 2/2001 | Thapliyal et al. |
| 6,200,280 | B1 | 3/2001 | Brenneman et al. |
| 6,245,077 | B1 | 6/2001 | East et al. |
| 6,251,121 | B1 | 6/2001 | Saadat |
| D450,843 | S | 11/2001 | McGuckin, Jr. et al. |
| 6,358,231 | B1 | 3/2002 | Schindler et al. |
| 6,440,102 | B1 | 8/2002 | Arenberg et al. |
| 6,475,138 | B1 | 11/2002 | Schechter et al. |
| 6,522,827 | B1 | 2/2003 | Loeb et al. |
| 6,645,173 | B1 | 11/2003 | Liebowitz |
| 6,770,080 | B2 | 8/2004 | Kaplan et al. |
| 6,916,159 | B2 | 7/2005 | Rush et al. |
| 7,127,285 | B2 * | 10/2006 | Henley et al. ............... 604/20 |
| D535,027 | S | 1/2007 | James et al. |
| 7,344,507 | B2 | 3/2008 | Briggs et al. |
| 7,351,246 | B2 | 4/2008 | Epley |
| 7,381,210 | B2 | 6/2008 | Zarbatany et al. |
| D595,410 | S | 6/2009 | Luzon |
| D598,543 | S | 8/2009 | Vogel et al. |
| D622,842 | S | 8/2010 | Benoist |
| 2002/0026125 | A1 | 2/2002 | Leysieffer |
| 2002/0069883 | A1 | 6/2002 | Hirchenbain |
| 2002/0169456 | A1 | 11/2002 | Tu et al. |
| 2003/0060799 | A1 | 3/2003 | Arenberg et al. |
| 2005/0182385 | A1 * | 8/2005 | Epley ....................... 604/514 |
| 2005/0235422 | A1 | 10/2005 | Wallace |
| 2005/0240147 | A1 | 10/2005 | Makower et al. |
| 2006/0155304 | A1 | 7/2006 | Kaplan et al. |
| 2007/0233222 | A1 | 10/2007 | Roeder et al. |
| 2008/0051804 | A1 | 2/2008 | Cottler et al. |
| 2008/0262468 | A1 | 10/2008 | Clifford et al. |
| 2009/0299344 | A1 | 12/2009 | Lee et al. |

FOREIGN PATENT DOCUMENTS

| | | |
|---|---|---|
| FR | 2526656 | 11/1983 |
| WO | WO 2006/119512 | 11/2006 |
| WO | WO 2008/030485 | 3/2008 |
| WO | WO 2008/036368 | 3/2008 |
| WO | WO 2009/010788 | 1/2009 |

OTHER PUBLICATIONS

Comeau, Maurice et al.; "Local Anesthesia of the Ear by Iontophoresis"; 1973, *Arch Otolaryngol*, vol. 98, pp. 114-120.

Echols, Dean F. et al.; "Anesthesia of the Ear by Iontophoresis of Lidocaine"; 1975, *Arch Otolaryngol*, vol. 101, pp. 418-421.

Epley, John M.; "Modified Technique of Iontophoretic Anesthesia for Myringotomy in Children"; 1977, *Arch Otolaryngol*, vol. 103, pp. 358-360.

Hasegawa, M. et al.; "Iontophoretic anaesthesia of the tympanic membrane"; 1978, *Clinical Otolaryngoloy*, vol. 3, pp. 63-66.

Ramsden, R.T. et al.; "Anaesthesia of the tympanic membrane using iontophoresis"; 1977, The Journal of Laryngology and Otology, vol. 56, No. 9, pp. 779-785.

U.S. Appl. No. 61/085,360.

U.S. Appl. No. 11/749,729.

U.S. Appl. No. 11/962,063.

U.S. Appl. No. 11/962,073.

International Search Report dated Sep. 3, 2008 re: PCT/US2008/60779.

International Search Report dated Nov. 6, 2009 for PCT/2009/052395.

U.S. Appl. No. 11/749,733, filed May 16, 2007.

Medtronic XOMED. Activent®, Antimicrobial Ventilation Tubes. 4 pages.

Micromedics Innovative Surgical Products [retrieved on Jul. 15, 2010] Retrieved from the Internet <URL: http://www.micromedics-usa.com/products/otology/micromedicstubes.htm. 7 pages.

International Search Report dated Jun. 30, 2010 re: PCT/US2009/069388.

International Search Report dated Aug. 27, 2010 re: PCT/US2010/042128.

International Search Report dated Feb. 17, 2011 re: PCT/US2010/058718.

* cited by examiner

IONTOPHORESIS METHODS

BACKGROUND OF THE INVENTION

The present invention is related to iontophoretic drug delivery methods and systems. In particular, the present invention is related to novel and advantageous iontophoretic drug delivery methods and systems for anesthetizing ear tissue.

Iontophoresis is a method for delivering a drug across a biological membrane, such as the skin or, in the case of certain ear surgery procedures, the tympanic membrane (TM). By applying low-level electrical current to a similarly charged drug solution, iontophoresis repels ions of the drug, thus transporting them across the skin or other membrane. In ear procedures, attempts have been made in the past to use iontophoresis to anesthetize (or "numb") a TM before placing an ear tube across it to treat chronic ear infections. For TM iontophoresis, a drug solution is placed in an ear canal and current is applied to the solution, thus transporting the anesthetizing drug across the TM.

In theory, iontophoresis should be ideal for numbing a TM, because it would allow drug to be transported across the full thickness of the TM, would focus the drug delivery on the TM and the surrounding ear canal, and would not require a painful injection with a needle. Iontophoretic drug delivery to the TM has proven challenging, however. Companies such as Xomed, Inc. (Medtronic Xomed, Inc.) and Otomed, Inc. (Lake Havasu City, Ariz.) have previously provided iontophoresis systems for anesthetizing TMs, but these systems and their associated methods have had a number of significant drawbacks. Most significantly, it has been very challenging, using previous iontophoresis systems, to provide adequate anesthesia to the TM without causing significant pain and discomfort to the patient in the process. Although the pain and discomfort caused by applying current to an iontophoretic solution in the ear canal may range from mild to severe, even mild pain or discomfort may make an ear tube placement procedure intolerable for pediatric patients and even some adult patients.

To drive a drug solution across a TM via iontophoresis, the solution must have certain characteristics to allow it to be transported, and current must be applied in such a way to cause the transport. Previously used iontophoresis solutions for TM anesthesia were generally mixtures of Lidocaine and epinephrine, often having a pH range of about 5.2-5.9, and this pH range was thought to be optimal for ionophoretic drug delivery. Once the solution is in place in the ear canal, a sufficient amount of current must be applied for a sufficient amount of time to transport the anesthetizing drug across the TM. Unfortunately, with previously available systems, the combinations of drug solution and current application were typically at least uncomfortable and often quite painful. Attempts to decrease the pain caused by iontophoresis generally resulted in unsatisfactory drug delivery.

Placement of ear tubes through the TMs for treating chronic ear infections is one of the most common ear, nose and throat ("ENT" or "otolaryngology") surgical procedures requiring general anesthesia in children. Although tube placement is a relatively routine procedure, it almost always requires general anesthesia when performed on children, since they are usually unable to tolerate the pain and discomfort associated with numbing the tympanic membranes for the procedure. Unfortunately, general anesthesia carries a number of risks, some of which are still unknown and being researched. Adult patients sometimes undergo ear tube placement with topical applications of local anesthesia (such as phenol), thus avoiding general anesthesia, but oftentimes such a procedure is quite painful or at least very uncomfortable, due to unsatisfactory methods of numbing the TMs. Therefore, it would be highly advantageous to provide a method for anesthetizing TMs and surrounding ear tissue that would eliminate the need for general anesthesia and that would be palatable to patients.

Therefore, a need exists for improved iontophoretic methods and systems. Ideally, such methods and systems would facilitate iontophoretic drug delivery across a tympanic membrane for ear tube placement or other surgical procedures in the ear. Also ideally, such methods and systems would minimize or eliminate any pain caused by the iontophoresis process. At least some of these objectives will be met by the various embodiments of the present invention.

BRIEF SUMMARY OF THE INVENTION

The present invention is directed to novel and advantageous iontophoretic drug delivery methods and systems, which may be used by ENT surgeons to anesthetize tympanic membranes (TMs). Various embodiments include means for providing simultaneous bilateral anesthetization of the TMs, reduction in patient discomfort via control of applied current, current density and ramp rate, allowance for intervention during the procedure by a physician, enhanced and real-time monitoring of the output current, and/or collection of the system's operational data.

In one embodiment, the present invention provides a method of anesthetizing a tympanic membrane of an ear of a patient using iontophoresis. The method may involve delivering an anesthetizing drug solution to an ear canal of the patient's ear, wherein the drug solution includes an anesthetic and a buffer, and wherein the drug solution has a pH in the range of about 6.5 to about 7.5; and applying an amount of current to the drug solution, wherein the amount of applied current is increased at a rate of less than about 0.5 milliamp per second until a maximum current is achieved.

In one aspect, the anesthetic may include Lidocaine and the buffer may include sodium bicarbonate, and wherein the solution also includes epinephrine. The drug solution may include approximately 2%-4% Lidocaine by weight. The drug solution may include approximately 0.5%-1.0% sodium bicarbonate by weight.

In one aspect, the drug solution may have a pH range of about 6.8-7.2.

In another aspect, the application of the current may involve increasing the amount of applied current at a rate of about 0.2 milliamp per second.

In another aspect, the application of the current may involve applying a maximum current of approximately 1.0 milliamp or less. In another aspect, the application of the current may involve applying a maximum current of approximately 0.8 milliamp or less.

In another embodiment, the present invention provides a method of anesthetizing a tympanic membrane of an ear of a patient using iontophoresis. The method may involve adding buffer to an anesthetizing drug solution for iontophoresis, wherein the drug solution with added buffer has a pH in the range of about 6.5 to about 7.5; delivering the buffered anesthetizing drug solution to an ear canal of the patient's ear; and applying an amount of current to the drug solution, wherein the amount of applied current is increased at a rate of less than about 0.5 milliamp per second until a maximum current of less than about 0.5 milliamp is achieved.

In one aspect, the buffered drug solution has a pH range of about 6.8-7.2.

In another aspect, the application of the current may involve increasing the amount of applied current at a rate of about 0.2 milliamp per second.

In another aspect, the application of the current may involve applying a maximum current of approximately 0.8 milliamp or less.

In another embodiment, the present invention provides a method of treating a patient, the patient having a first and a second ear canal. The method may involve positioning a fluid in the first ear canal, the fluid comprising a therapeutic agent; positioning a fluid in the second ear canal, the fluid comprising a therapeutic agent; inserting a first electrode of an iontophoresis device in the first ear canal; inserting a second electrode of the iontophoresis device in the second ear canal; attaching one ground electrode of the iontophoresis device to the patient, the first electrode and the one ground electrode forming a first circuit, the second electrode and the same one ground electrode forming a second circuit; applying the agent from the fluid to a target tissue in the first ear canal by energizing the first circuit to deliver a current to the agent in the first ear canal; and applying the agent from the fluid to a target tissue in the second ear canal by energizing the second circuit to deliver a current to the agent in the second ear canal, independently of the applying in the first circuit.

In one aspect, the agent may include an anesthetic.

In another aspect, the agent may include at least one of lidocaine, epinephrine, sodium bicarbonate, other anesthetics, other buffers, or combinations thereof.

In another aspect, the agent may include at least one of an antibiotic, an anti-inflammatory, a mucolytic, an anesthetic, a steroid, an anti-viral, a surfactant or combinations thereof.

In another aspect, the energizing of the first or the second circuit may include applying a current to the agent over a time period, the current having an initial value, a final value, a ramp-up rate from the initial value to the final value and a ramp-down rate from the final value to the initial value. The ramp-up rate is about 0.2 milliamp per second. The ramp-up rate may have a stepped and positive slope. The final value may be less than about 1.0 milliamp. The period of time may be between about 30 and 240 seconds.

In another aspect, the method may also involve pausing the application of the agent during the application.

In one aspect, the fluid is an iontophoretic solution of lidocaine and epinephrine that is buffered to have a pH of about 6.8-7.2.

In another aspect, the iontophoretic solution may have a lidocaine HCl concentration between approximately 2%-4% by weight.

In another aspect, the method may also include monitoring the first or the second circuit's output current. In one aspect, the monitoring may involve comparing the output current with a threshold value. In another aspect, the monitoring may be performed at a rate of at least once per second.

In another embodiment, the present invention provides an iontophoresis system for anesthetizing a tympanic membrane of an ear of a patient. The system may include an anesthetizing drug solution including an anesthetic and a buffer and having a pH in the range of about 6.5 to about 7.5; a current source; and a controller coupled with the current source, the controller programmed to increase an amount of current applied to the drug solution at a rate of less than about 0.5 milliamp per second until a maximum current of less than about 1.0 milliamp is achieved.

In one aspect, the anesthetizing drug solution may include an anesthetic, epinephrine and a buffer. The drug solution may have approximately 2%-4% of Lidocaine by weight and approximately 0.5%-1.0% of sodium bicarbonate by weight.

In another aspect, the drug solution may have a pH range of about 6.8-7.2.

In another aspect, the controller may be programmed to increase the amount of current applied to the drug solution at a rate of about 0.2 milliamp per second until a maximum current of about 0.8 milliamp is achieved.

In another aspect, the current source may include at least one ear electrode configured for placement in an ear canal of the patient.

In another aspect, the current source may include two ear electrodes configured for placement in two ear canals of the patient, thus allowing for approximately simultaneous application of current to anesthetizing drug solution disposed in the two ear canals.

For further understanding of the nature and advantages of the various embodiments, reference should be made to the following description taken in conjunction with the accompanying figures. Each of the figures is provided for the purpose of illustration and description only and is not intended to limit the scope of the embodiments of the present invention.

DETAILED DESCRIPTION OF THE INVENTION

According to various embodiments, an iontophoresis method and system may provide ear, nose and throat ("ENT") surgeons (also called "otolaryngologists") with an improved means for anesthetizing tympanic membranes (TMs). An exemplary iontophoresis system that may be enhanced using embodiments of the present invention is described in the assignee's copending patent application Ser. No. 11/749,729, entitled "Disposable Iontophoresis System and Tympanic Membrane Pain Inhibition Method," which is incorporated fully herein by reference. Certain aspects of that system are described below.

Figure 1:
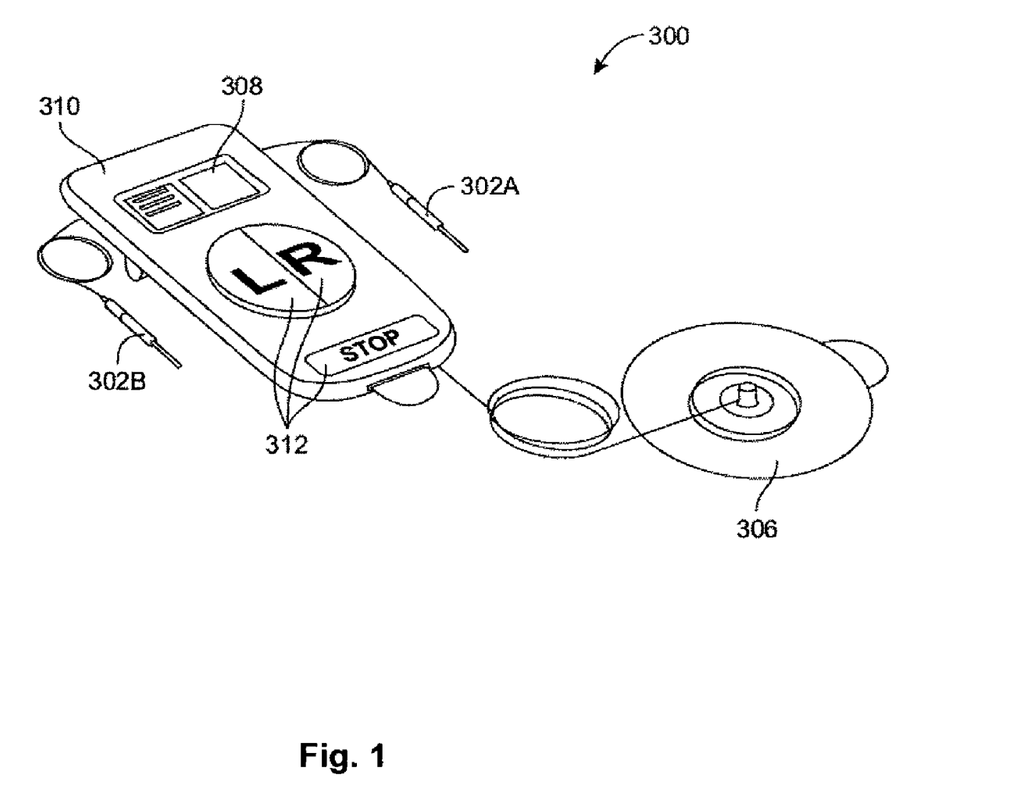
FIG. 1 illustrates an exemplary iontophoresis system, according to one embodiment of the present invention.
Figure 2:
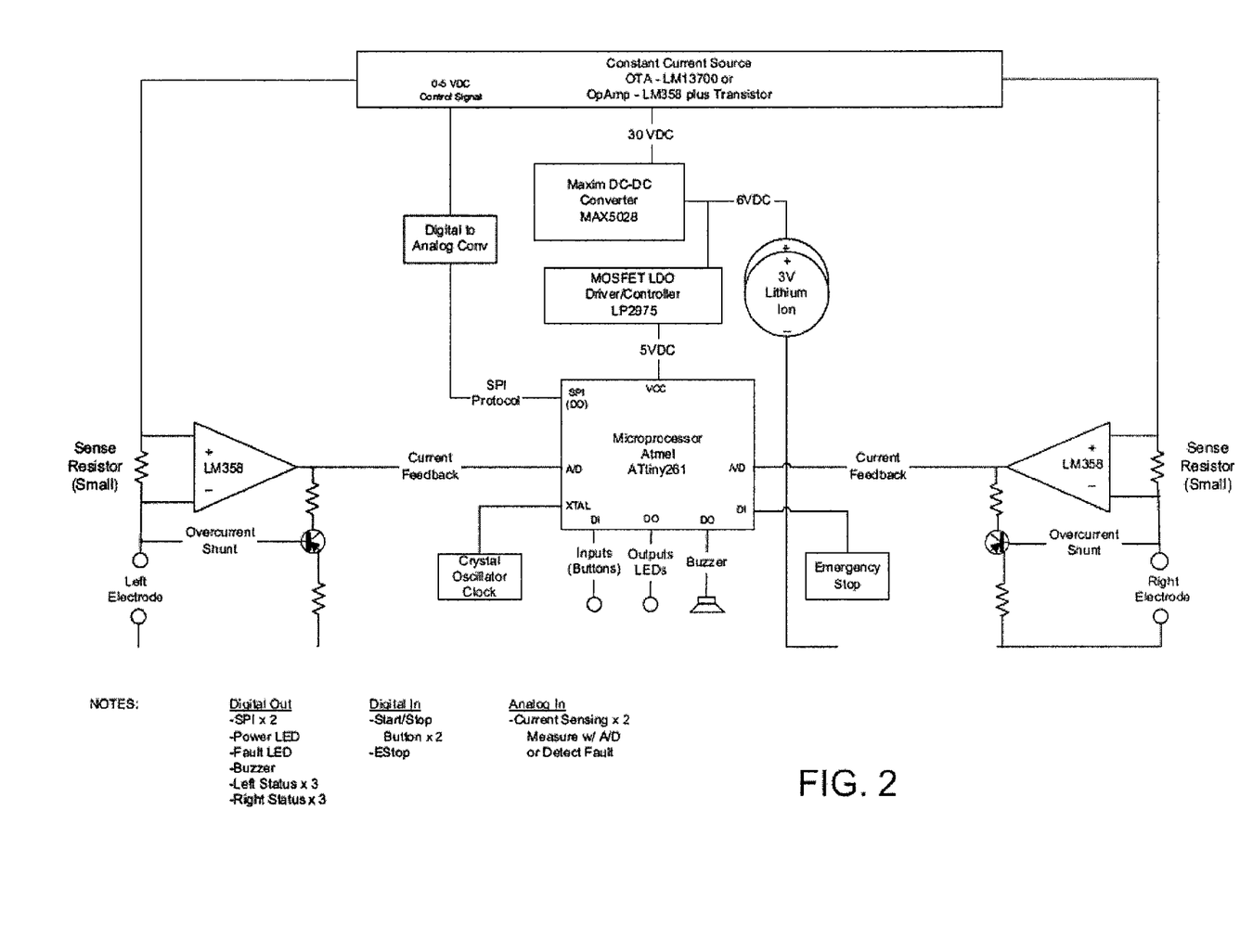
FIG. 2 is an exemplary circuit diagram illustrating the electronic architecture of the iontophoresis system of FIG. 1.

FIGS. 1-2 are used to illustrate various aspects of an iontophoresis system 300, according to one embodiment. As shown in FIG. 1, iontophoresis system 300 may include a battery powered disposable electronic device 310 having an LCD display 308 one or more buttons 312 for operation, two electrodes (one for each ear) 302A-B couplable with device 310, and a return electrode patch 306 couplable with device 310. Device 310 may be configured to deliver regulated current to electrodes 302A-B. Each electrode 302A-B may be configured to fit within an external ear canal or a guide block that is positioned in the ear canal. Each electrode 302A-B may be configured to conform to the shape of a patient's ear canal and thus retain a drug solution in the canal while delivering electrical current to the solution. Various embodiments of electrodes 302A-B may be sized to fit patients ranging in age from 12 months to adult. Return electrode 306 may be attached to the patient's skin to complete the electrical circuit. As shown in FIG. 1, the iontophoresis system 300 may be a small electronic device, in various embodiments ranging from about the size of a business card to the size of an iPod™ or personal digital assistant. In one embodiment, device 310 may be co-located with return electrode patch 306 to minimize the amount of loose wires and overall package size. In this embodiment, return electrode patch 306 may be attached permanently or by means of a metal snap or other electrically conductive attachment mechanism to device 310, and device/patch 310/306 may be adhered to the patient's skin (e.g. at the back of the neck) via return electrode patch 306, thereby fixing the device 310 in a location easily accessible to the physician but not easily accessible to the patient.

In one embodiment, iontophoresis system 300 may be activated by pulling a small plastic tab (not shown) from the back of device 310. Such a tab may be configured to keep batteries installed in device 310 from powering the device circuitry until desired. When the tab is pulled, the batteries begin powering the circuitry and the LCD 308 may illuminate. In alternative embodiments, any other suitable means for powering device 310 may be included, such as a power switch or button.

In various embodiments, device 310 may be powered before or after applying return electrode 306 to the patient. At some point, a solution is placed in the patient's ear canal, an electrode 302A-B is placed in the canal, and electrode 302A-B is used to apply current to the solution. In some embodiments, electrode 302A-B may be placed in the canal before solution is placed, and the solution may then be passed into the canal through or around electrode 302A-B, such as when a guide block is used. In some embodiments, solution may be placed in one ear, an electrode 302A may be positioned in that ear canal, solution may be placed in the other ear, an electrode 302B may be placed in that ear, and then iontophoresis may be performed on both ears simultaneously, almost simultaneously, or sequentially. Alternatively, a left electrode 302A may be placed first, and a "Left Ear Start" button on device 310 may be pressed to begin an automatic, pre-programmed current delivery sequence. A right ear electrode 302B may then be placed into the patient's right ear canal and a "Right Ear Start" button may be pressed to independently begin current delivery to the right ear. In some embodiments, a progress meter may be displayed for each ear on LCD 308. For example, a progress meter may be represented by a filled-in area of a box, which starts empty and fills in as current is delivered until is it fully filled and the process is complete. Once current delivery starts, the user can wait for the device to signal it is finished or there is a problem via an auditory beep sound. After the device delivers the full dosage of current to each ear, the progress meter for each ear is filled and the system can deliver a short series of beeps to signal successful completion. Once the device signals it is completed it can automatically shut down. At this point, the user can remove the electrodes, and can start the process of removing any iontophoresis solution remaining in the ear canal. Again, this can be done independently on one side without affecting proper device operation on the other side.

At any time during the process, the current delivered to an electrode can be paused, for example by pressing the left or right button. The system can then ramp down the current to that electrode. The user can also pause both electrodes at once, for example by pressing the stop button. This will cause the system to ramp down the current to both electrodes. In either case the user can continue with the procedure by pressing the left or right buttons. This will cause the system to ramp up the current for that electrode and continue delivering the total charge where it left off before being paused. In one embodiment, the same button may be used for starting, pausing and stopping current delivery to an electrode, while in alternative embodiments separate start, pause and/or stop buttons may be included.

At the end of the iontophoresis current delivery cycle, the current will ramp down to zero. Once both sides have completed iontophoresis and the electrodes have been removed, the return patch can also be removed and the entire unit discarded. Power can automatically shut off after one hour of time, or any selected unit of time. The unit can be designed to allow only one use and can not be turned back on. Another embodiment disables the current delivery function after a single use, but then enables additional functionality, such as a game, a clock, etc. for the patient's use after the procedure.

In some embodiments, if an error occurs during a procedure, the system may emit an indicator signal, such as a series of long beeps. Alternatively, or in addition to the series of long beeps, visual means may be used, so as not to disturb the patient. For example, a blinking light located on the back of the unit or other hard to reach place would likely not be noticed by patient. Conditions that could cause such an error include: a detected open circuit or an over current condition. In the case of an open circuit, the device may automatically stop delivering current to the patient through a controlled current ramp down and the user may resume delivery by pressing a start button on the device. In the case of over current, the device may detect an internal error, automatically stop all current to both electrodes, and not restart, at which point the device may be discarded. In some embodiments, an indicator message may be displayed on LCD screen 308.

Referring now to FIG. 2, a circuit diagram illustrating one embodiment of an electronic architecture for iontophoresis system 300 is shown. In one embodiment, once the plastic tab is removed from the back of device 310, two 3V batteries begin to power the circuit. The batteries may supply a LP2975 voltage regulator, which delivers a stable 5V output. The 5V output is used to supply the microprocessor (e.g., Atmel ATtiny 261), the digital-to-analog converter (DAC) converter (e.g., Maxim MCP4922), the current sensing operational amplifiers (e.g., LM358), and all components of the operator interface (buttons, buzzer, LCD). The microprocessor controls the majority of the functions of the emergency stop button to ramp down current to both electrodes; analog inputs for sensing current delivered to each electrode; serial peripheral interface (SPI) communications to set reference for the DAC; control signals for buzzer and LCD. External to the microprocessor, the 6V battery power drives the MAX5028 DC-DC converter which converts the battery voltage to a 30V output. This output is used as the rail power for the constant current unit. The constant current unit can be designed using one of two alternatives. The first alternative uses an Operational Amplifier (Op-Amp) such as LM358 which converts a differential input voltage (the control signal) to an output voltage, and eventually to a current based on the chosen sense resistor. The second technique uses Operational Transconductance Amplifiers (OTA) which operate in a manner similar to an Op-Amp in that it is controlled by a differential input voltage, but it drives an output current based on a biasing current provided externally.

The microprocessor sets a reference voltage level to the current source using a DAC. The microprocessor communicates to the DAC via a serial protocol SPI. The constant current source uses a control signal (0-5V) from the microprocessor to ramp 0 to 1 mA of current according to a predetermined ramp shape. The DC-DC converter provides a high enough rail voltage (30V) to allow the constant current source to drive 1 mA of current based on a maximum expected body resistance of 22.5 kOhms. After the allotted delivery time, the microprocessor ramps the control signal back down to 0V, which reduces the current delivered by the current source back to zero.

The system may include an LM358 Op-Amp on each electrode line to measure the current delivered to the patient. The Op-Amps are connected to analog-to-digital converters internal to the microprocessor. This gives feedback information to the microprocessor for sensing of open circuits within the electrode circuit and to calculate total charge delivered to the patient. For safety, the current sensing Op-Amps in parallel with the output electrode also drive an over current monitor. If a fault occurs and current increases beyond a set limit of 1.5 mA due to some internal failure, the transistor in the over current shunt will open and allow the increased current to bypass the load, the patient in this case, and safely return to the cathode (negative terminal) of the battery. The microprocessor will independently detect the over current condition, shut down the current source, and inform the operator of a system fault.

After the system has completed delivering the total charge to the patient it can go into a finished state and begin a timeout count. At the end of the timeout count, the firmware may turn off the system such that it cannot be turned back on. The microprocessor may include EEPROM memory written to when the system is turned on initially. If the system is re-powered, for instance, by forcibly replacing the batteries, the firmware can detect that it has been powered before and could not turn on again. This scheme is to ensure the device is used only one time. The microprocessor includes internal brown-out detection to detect if the system voltage is below nominal. This detection is used by the firmware to disallow the system to begin or complete operation if the system does not have enough power (e.g. if the batteries are drained).

As described above, the iontophoresis generator may provide two independent channels of positive electrical current and a single shared return electrode. Current may be ramped up to a set point and maintained until sufficient charge has been delivered to the drug solution. The current may then be ramped down, and the system may inform the physician that current delivery is complete. In various embodiments, the physician may stop or pause the procedure at any time. In some embodiments, the physician may stop the procedure immediately (i.e., without ramping down current delivery) by simply removing the electrode from the ear canal.

Thus, in some embodiments, the iontophoresis system has two independent channels, each with its own ear electrode and sharing a single common return electrode. This allows each TM to be anesthetized independently but also at the same time, decreasing the amount of time required for the procedure. The simultaneous bilateral delivery of iontophoresis can cut the procedure time roughly in half when compared with how the existing devices are used. This is especially useful in reducing the time children are asked to sit still and tolerate devices in their ears.

Figure 4:
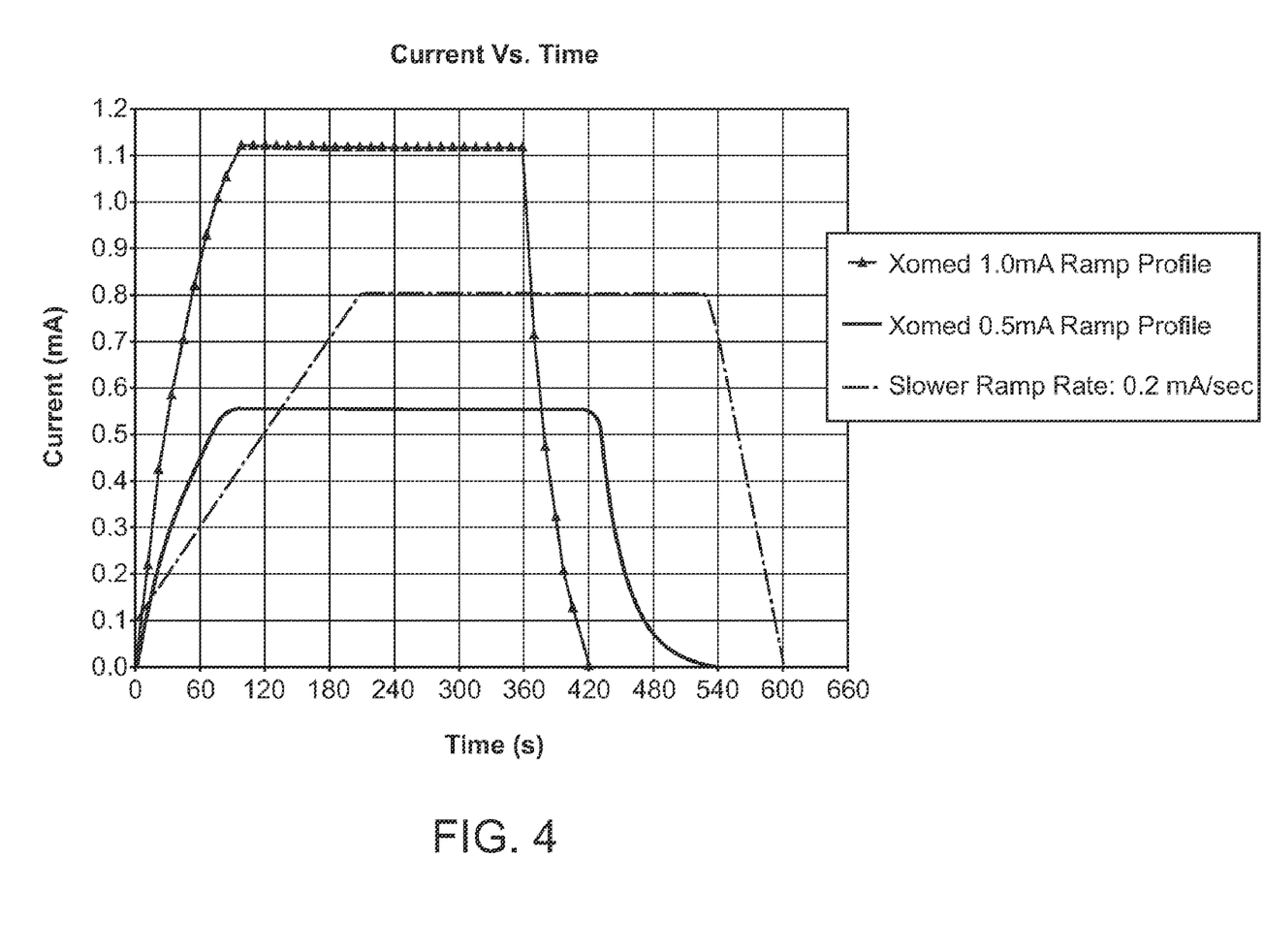
FIG. 4 illustrates an exemplary current ramp rate for an iontophoresis system, according to one embodiment of the present invention.

Referring now to FIG. 4, in some embodiments, current ramp rate of an iontophoresis method may be configured to minimize or eliminate patient pain and discomfort while still providing sufficient current to transport a drug solution across a TM within a desired amount of time. In some embodiments, an iontophoresis method may involve a slower current "ramp rate" (rate at which the amount of delivered current is increased) and thus a longer current ramp-up period. In some embodiments, for example, delivered current may increase from zero at a rate of less than about 0.5 mA/sec and even more ideally at a rate of about 0.2 mA/sec. In some embodiments, total ramp-up time (from zero current delivered to maximum current delivered) may be from about 2 minutes to about minutes and even more ideally from about 3 minutes to about 4 minutes. Maximum current delivered may vary according to various embodiments, for example in some embodiments it may range from about 0.5 mA to about 1.0 mA and even more preferably between about 0.7 mA and about 0.9 mA and even more preferably about 0.8 mA. The maximum current may be maintained for any suitable desired amount of time to achieve TM anesthesia, such as from less than one minute to over ten minutes and in some embodiments for example from about five minutes to about eight minutes. Any suitable ramp-down time for the current may be used at the end of iontophoretic current delivery, such as in one embodiment from less than one minute to about two minutes. In one embodiment, a total time for iontophoresis of one TM may take between about five minutes and about fifteen minutes and even more preferably between about seven minutes and about twelve minutes.

In some embodiments, the iontophoresis system may be configured to allow a physician to easily respond to patient discomfort by pausing or ramping down the device. For example, pressing a single button may pause the current ramp-up until the physician presses the button again. Pressing a single button for a longer period of time may ramp the current output back down to zero and may keep track of the charge delivered, allowing the physician to resume the procedure instead of starting over.

In some embodiments, a drug solution provided for TM iontophoresis may be configured to minimize or eliminate pain and discomfort. Because it has been found that iontophoresis current delivered through an acidic iontophoresis solution may be more painful than current delivered through a more neutral solution, in some embodiments a solution with a more neutral pH may be provided. In one embodiment, for example, a buffer may be added to a conventional iontophoresis solution of Lidocaine and epinenphrine. Examples of buffers that may be used include but are not limited to sodium bicarbonate. For example, some previously used iontophoresis solutions may have included Lidocaine (4%) and Epinephrine (1:1000), with a pH in the range between 5.2-5.9. Epinephrine is packaged in an acidic solution (e.g., ~3.0 pH) to extend its shelf life, but it is stable at higher pH levels for the duration of time that iontophoresis takes place. Therefore, in one embodiment, just prior to use, an iontophoresis solution may be buffered to a neutral pH with sodium bicarbonate or some other buffer.

In some embodiments, where a buffer is included in an iontophoresis solution, the solution may also include a higher Lidocaine concentration than in previously used solutions. Since a buffer may slow the rate at which the solution is driven across the TM, increasing the Lidocaine concentration may make up for this slowing by increasing the percentage of ionized lidocaine molecules in the buffered iontophoresis solution. For example, an unadjusted iontophoresis solution may comprises a solution of 1:2000 epinephrine and 2% Lidocaine HCl, having a pH between approximately 5.2-5.9. When the solution is buffered to a neutral pH of about 7, the degree of ionization of Lidocaine will decrease. Since iontophoresis uses electrical current to push ionized molecules across a biological membrane such as the TM, the buffering will cause a decrease in Lidocaine flux due to the increased pH. One way to balance this decrease in iontophoresis transport is to increase the amount of ionized molecules in the starting solution by increasing the concentration of Lidocaine. For example, if the iontophoretic solution started with a 3.3% lidocaine HCl concentration instead of 2%, then even a loss of 20% of the ionized molecules by raising the pH to 7, will result in a solution having a 2.6% lidocaine HCl concentration. Accordingly, in various embodiments, the solution may have up to 4% lidocaine HCl, as this amount has been determined to be safe for iontophoretic purposes. In some embodiments, the amount of epinephrine in solution may also be adjusted.

In one embodiment, an iontophoresis system may be configured to deliver a maximum output per channel of about 30 volts. In one embodiment, an iontophoresis system may be configured to monitor the actual current output and calculate the charge delivered. In one embodiment, output current may be monitored in a fault-tolerant manner. For this, the output current may be compared to the intended current several times a second. Then when the measured output current is outside of the allowable range, a "strike" is recorded. If a certain number of strikes accumulates within a block of time, the user may be alerted that the system needs to be checked.

In one embodiment of an iontophoresis method, the current being delivered to each channel may be ramped up in steps, such that the current set point is raised to a value, maintained for a certain amount of time, and then raised again. This method of ramping the current up or down may help facilitate current monitoring. In another embodiment, output of the iontophoresis device may be recorded. For example, output voltage, output current, and/or setpoint current of each channel may be sent to a data acquisition system and recorded over the course of the procedure, without interfering with the current supplied to the patient. In one embodiment, from this data, changes in body resistance and power output may be calculated.

Figure 3:
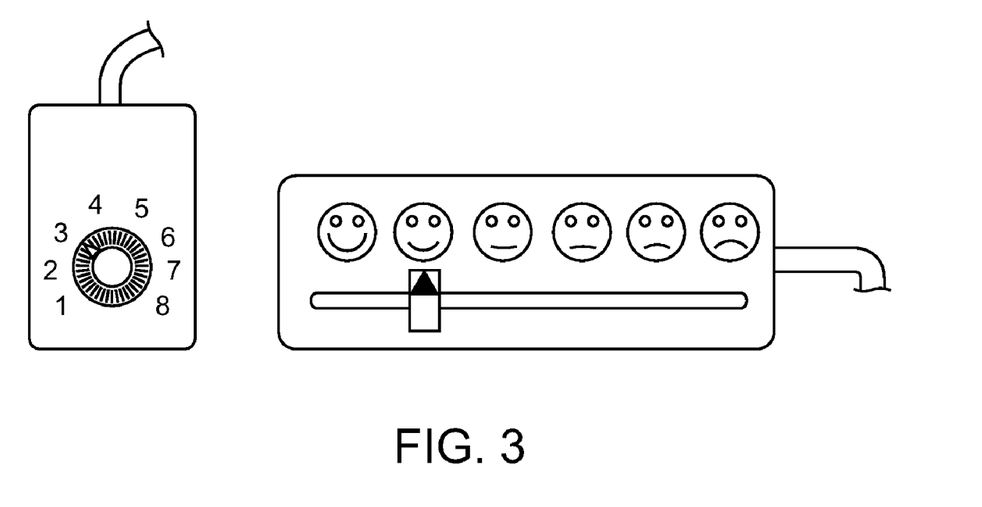
FIG. 3 illustrates exemplary sensometers that may be operatively coupled with an iontophoresis system, according to one embodiment of the present invention.

In one embodiment, an iontophoresis system may further be configured to record patient discomfort continuously over the course of the procedure using a sensometer as shown in FIG. 3. As shown in FIG. 3, the patient can adjust a dial 402 or slider 404, which can correspond to a pain level. The scale can use a numeric range as in dial 402 or a more user friendly scale that shows a face pain scale may be used. The dial or slider is attached to a potentiometer such that the output voltage or current is correlated with a pain level. Patient discomfort could be compared second by second with the electrical output to better inform subsequent current delivery settings to reduce patient discomfort. The sensometer can be operatively connected with the iontophoresis generator. The iontophoresis generator could then monitor the patient's level of discomfort and adjust the output accordingly, such as temporarily reducing output current until the patient felt better. The data may be recorded alongside the output of the iontophoresis machine.

The present invention may be embodied in other specific forms without departing from the essential characteristics thereof. These other embodiments are intended to be included within the scope of the present invention, which is set forth in the following claims.

What is claimed is:

1. A method of anesthetizing tympanic membranes in a patient, the patient having a first and a second ear canal, the method comprising:
   delivering an amount of an anesthetizing drug solution to the first ear canal, wherein the drug solution includes an anesthetic and a buffer, and wherein the drug solution has a pH in the range of about 6.5 to about 7.5;
   delivering an additional amount of the anesthetizing drug solution to the second ear canal;
   inserting a first electrode of an iontophoresis device in the first ear canal to contact the anesthetizing drug solution;
   inserting a second electrode of the iontophoresis device in the second ear canal to contact the anesthetizing drug solution;
   attaching a ground electrode of the iontophoresis device to the patient, the first electrode and the ground electrode forming a first circuit, the second electrode and the ground electrode forming a second circuit;
   energizing the first circuit to deliver a current to the anesthetizing drug solution in the first ear canal via the first electrode to cause at least some of the drug solution to pass into a first tympanic membrane;
   energizing the second circuit to deliver a current to the anesthetizing drug solution in the second ear canal via the second electrode to cause at least some of the drug solution to pass into a second tympanic membrane, independently of energizing the first circuit and while energizing the first circuit;
   independently increasing the current delivered to the first and second electrodes at a ramp-up rate of about 0.2 milliamp per second until a maximum delivered current is achieved in each electrode; and
   displaying a progress meter for each of a left and right ear indicating delivery of the current to the anesthetizing drug solution for each of the left and right ear.

2. The method of claim 1, wherein the anesthetic comprises lidocaine and the buffer comprises sodium bicarbonate, and wherein the solution further comprises epinephrine.

3. The method of claim 2, wherein the drug solution includes approximately 2%-4% lidocaine by weight.

4. The method of claim 3, wherein the drug solution includes approximately 0.5%-1.0% sodium bicarbonate by weight.

5. The method of claim 1, wherein the anesthetizing drug solution comprises at least one of lidocaine, epinephrine, sodium bicarbonate, other anesthetics, other buffers, and combinations thereof.

6. The method of claim 1, wherein the anesthetizing drug solution comprises at least one of an antibiotic, an anti-inflammatory, a mucolytic, a steroid, an anti-viral, a surfactant or combinations thereof.

7. The method of claim 1, wherein said energizing and increasing comprise applying the current to the anesthetizing drug solution over a time period, said current having an initial value, the ramp-up rate from said initial value to said maximum value and a ramp-down rate from said maximum value to said initial value.

8. The method of claim 7, wherein said ramp-up rate comprises a stepped and positive slope.

9. The method of claim 8, wherein said current having a final value, said final value is less than about 1.0 milliamp.

10. The method of claim 9, wherein said final value is approximately 0.8 milliamp or less.

11. The method of claim 7, wherein said period of time is between about 30 and 240 seconds.

12. The method of claim 1, further comprising pausing at least one of the energizing steps.

13. The method of claim 1, wherein said anesthetizing drug solution is an iontophoretic solution of lidocaine and epinephrine that is buffered to have a pH of about 6.8-7.2.

14. The method of claim 13, wherein said iontophoretic solution has a lidocaine HCl concentration between approximately 2%-4% by weight.

15. The method of claim 1, further comprising monitoring the first or the second circuit's output current.

16. The method of claim 15, wherein said monitoring comprises comparing the output current with a threshold value.

17. The method of claim 15, wherein said monitoring is performed at a rate of at least once per second.

18. A method of anesthetizing tympanic membranes in a patient, the patient having a first and a second ear canal, the method comprising:
- delivering an amount of an anesthetizing drug solution to the first ear canal, wherein the drug solution includes an anesthetic and a buffer, and wherein the drug solution has a pH in the range of about 6.5 to about 7.5;
- delivering an additional amount of the anesthetizing drug solution to the second ear canal;
- inserting a first electrode of an iontophoresis device in the first ear canal to contact the anesthetizing drug solution;
- inserting a second electrode of the iontophoresis device in the second ear canal to contact the anesthetizing drug solution;
- attaching a ground electrode of the iontophoresis device to the patient, the first electrode and the ground electrode forming a first circuit, the second electrode and the ground electrode forming a second circuit;
- energizing the first circuit to deliver a current to the anesthetizing drug solution in the first ear canal via the first electrode to cause at least some of the drug solution to pass into a first tympanic membrane;
- energizing the second circuit to deliver a current to the anesthetizing drug solution in the second ear canal via the first electrode to cause at least some of the drug solution to pass into a second tympanic membrane, independently of energizing the first circuit and while energizing the first circuit;
- independently increasing the current delivered to the first and second electrodes at a ramp-up rate of about 0.2 milliamp per second until a maximum delivered current is achieved in each electrode; and
- receiving a signal correlated within pain level and modifying the current delivered to the first and second electrodes in response, the signal being controlled by the patient.

19. The method of claim 18, wherein the anesthetic comprises lidocaine and the buffer comprises sodium bicarbonate, and wherein the solution further comprises epinephrine.

20. The method of claim 19, wherein the drug solution includes approximately 2%-4% lidocaine by weight.

21. The method of claim 20, wherein the drug solution includes approximately 0.5%-1.0% sodium bicarbonate by weight.

22. The method of claim 18, wherein the anesthetizing drug solution comprises at least one of lidocaine, epinephrine, sodium bicarbonate, other anesthetics, other buffers, and combinations thereof.

23. The method of claim 18, wherein the anesthetizing drug solution comprises at least one of an antibiotic, an anti-inflammatory, a mucolytic, a steroid, an anti-viral, a surfactant or combinations thereof.

24. The method of claim 18, wherein said energizing and increasing comprise applying the current to the anesthetizing drug solution over a time period, said current having an initial value, the ramp-up rate from said initial value to said maximum value and a ramp-down rate from said maximum value to said initial value.

25. The method of claim 24, wherein said ramp-up rate comprises a stepped and positive slope.

26. The method of claim 25, wherein said current having a final value, said final value is less than about 1.0 milliamp.

27. The method of claim 26, wherein said final value is approximately 0.8 milliamp or less.

28. The method of claim 24, wherein said period of time is between about 30 and 240 seconds.

29. The method of claim 18, further comprising pausing at least one of the energizing steps.

30. The method of claim 18, wherein said anesthetizing drug solution is an iontophoretic solution of lidocaine and epinephrine that is buffered to have a pH of about 6.8-7.2.

31. The method of claim 30, wherein said iontophoretic solution has a lidocaine HCl concentration between approximately 2%-4% by weight.

32. The method of claim 18, further comprising monitoring the first or the second circuit's output current.

33. The method of claim 32, wherein said monitoring comprises comparing the output current with a threshold value.

34. The method of claim 32, wherein said monitoring is performed at a rate of at least once per second.

* * * * *